United States Patent
Cadra et al.

(10) Patent No.: US 11,335,954 B2
(45) Date of Patent: May 17, 2022

(54) IONIC LIQUID-BASED ELECTROLYTES FOR USE IN ELECTROCHEMICAL STORAGE DEVICES

(71) Applicant: COMMISSARIAT À L'ÉNERGIE ATOMIQUE ET AUX ÉNERGIES ALTERNATIVES, Paris (FR)

(72) Inventors: Stéphane Cadra, Saint Avertin (FR); Jonathan Szymczak, Quimper (FR); Matthieu Le Digabel, Monts (FR); Agnès Biller, Saint-Avertin (FR)

(73) Assignee: COMMISSARIAT À L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 225 days.

(21) Appl. No.: 16/495,197

(22) PCT Filed: Mar. 21, 2018

(86) PCT No.: PCT/FR2018/050683
§ 371 (c)(1),
(2) Date: Sep. 18, 2019

(87) PCT Pub. No.: WO2018/172697
PCT Pub. Date: Sep. 27, 2018

(65) Prior Publication Data
US 2020/0020984 A1    Jan. 16, 2020

(30) Foreign Application Priority Data

Mar. 23, 2017 (FR) ........................................ 1752435

(51) Int. Cl.
| | | |
|---|---|---|
| *H01M 10/0569* | (2010.01) | |
| *H01M 10/0568* | (2010.01) | |
| *C07D 295/00* | (2006.01) | |
| *C07D 223/04* | (2006.01) | |
| *C07D 221/00* | (2006.01) | |
| *C07D 207/00* | (2006.01) | |
| *H01M 4/587* | (2010.01) | |
| *H01M 10/0525* | (2010.01) | |
| *C07C 317/04* | (2006.01) | |
| *C07D 207/06* | (2006.01) | |

(52) U.S. Cl.
CPC ....... *H01M 10/0569* (2013.01); *C07C 317/04* (2013.01); *C07D 207/00* (2013.01); *C07D 207/06* (2013.01); *C07D 221/00* (2013.01); *C07D 223/04* (2013.01); *C07D 295/00* (2013.01); *H01M 4/587* (2013.01); *H01M 10/0525* (2013.01); *H01M 10/0568* (2013.01)

(58) Field of Classification Search
None
See application file for complete search history.

(56) References Cited

U.S. PATENT DOCUMENTS

| | | | |
|---|---|---|---|
| 10,026,993 B2 | 7/2018 | Srour et al. | |
| 2004/0094741 A1* | 5/2004 | Sato .................. | H01M 10/0568 252/1 |
| 2010/0304225 A1* | 12/2010 | Pascaly ................. | H01G 11/62 429/342 |
| 2011/0206979 A1* | 8/2011 | Giroud .............. | H01M 10/4235 429/162 |
| 2015/0340738 A1 | 11/2015 | Moganty et al. | |

FOREIGN PATENT DOCUMENTS

| | | |
|---|---|---|
| EP | 2549577 A1 | 1/2013 |
| FR | 3002086 A1 | 8/2014 |
| WO | 2010023185 A1 | 3/2010 |

OTHER PUBLICATIONS

Search Report for French Application No. FR1752435 dated Aug. 25, 2017.
International Search Report for PCT/FR2018/050683 dated May 30, 2018.
Written Opinion for PCT/FR2018/050683 dated May 30, 2018.
Seki, S. et al."Compatability of N-Methyl-N-propylpyrrolidinium Cation Room-Temperature Ionic Liquid Electrolytes and Graphite Electrodes" IN: Journal of Physical Chemistry C, Oct. 1, 2008, vol. 112. No 42, pp. 16708-16713.
Kim, G. T. et al. "Development of ionic liquid-based lithium battery prototypes" IN: Journal of Power Sources, 2012, vol. 199, pp. 239-246.
Lu, Jiong et al. "One-Pot Synthesis of Fluorescent Carbon Nanoribbons, Nanoparticles, and Graphene by the Exfoliation of Graphite in Ionic Liquids" IN: ACS nano, Aug. 5, 2009, vol. 3, No. 8, pp. 2367-2375.
Holzapfel, M. et al. "Stabilisation of lithiated graphite in an electrolyte based on ionic liquids: an electrochemical and scanning electron microscopy study" IN: Carbon, Jun. 2005, vol. 43, No. 7. pp. 1488-1498.

* cited by examiner

*Primary Examiner* — Ula C Ruddock
*Assistant Examiner* — Anna Korovina
(74) *Attorney, Agent, or Firm* — Pearne & Gordon LLP

(57) ABSTRACT

Electrolytes comprising at least one lithium salt and at least two ionic liquids, at least one of which is an ionic liquid resulting from the association of at least one cation complying with the following formula (I):

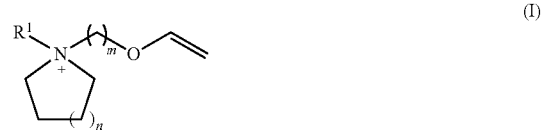

In which: $R^1$ is an acyclic hydrocarbon group; n is an integer ranging from 0 to 3; m is an integer ranging from 1 to 4; and at least one Y anion.

18 Claims, No Drawings

IONIC LIQUID-BASED ELECTROLYTES FOR USE IN ELECTROCHEMICAL STORAGE DEVICES

CROSS-REFERENCE TO RELATED APPLICATIONS

This is a National Stage application of PCT international application PCT/FR2018/050683, filed on Mar. 21, 2018, which claims the priority of French Patent Application No. 17 52435, filed Mar. 23, 2017, both of which are incorporated herein by reference in their entireties.

TECHNICAL FIELD

The present invention relates to new electrolytes based on at least two ionic liquids and at least one lithium salt, these electrolytes benefiting in particular from a sub-ambient melting point and high ionic conductivity (for example above 1 mS/cm). Furthermore, at least one of the specific ionic liquids forming part of the composition of the electrolytes of the invention has a stabilising function vis-à-vis certain materials conventionally used for forming electrodes, such as graphite electrodes. Such electrolytes also are of interest for use in secondary batteries, in particular because of the low losses in capacity during operation of said batteries and good efficiency of restitution of the energy stored during charging (that is to say, in other words, good coulombic efficiency).

Thus, because of all their electrochemical properties, the electrolytes of the invention can find an application in all fields relating to the electrochemical storage of energy, such as accumulators (or secondary batteries) or, more specifically, accumulators involving at least one graphite-based electrode.

Ionic liquids are specific salts in the liquid state at ambient temperature (the melting point being lower than ambient temperatures, for example 20° C.), unlike conventional salts, such as sodium chloride, which have a melting point of around 180° C., these ionic liquids being able to be represented by the following general formula:

$$A^+ X^-$$

in which:
  $A^+$ represents a cation, such as a phosphonium cation or a quaternary ammonium cation; and
  $X^-$ represents an organic anion, such as an imidide anion.

The particularity of ionic liquids in terms of state results, in particular, from the morphological difference between the anion and the cation (for example, with regard to steric hindrance and geometry), which is unfavourable to the establishment of a crystalline form of the salt.

Furthermore, ionic liquids have low toxicity, very low flammability, electrochemical stability and advantageous ionic conductivity.

Because of this, ionic liquids are highly advantageous in the fields requiring the use of conductive solutions of ions and may in particular be used as electrolytes in energy storage devices, such as second-generation security batteries, such as lithium-sulfur batteries, lithium-ion batteries or redox flow batteries.

Among all existing ionic liquids, the most widespread and most used for use in batteries are of the N,N'-methyl-alkyl pyrrolidinium bis(trifluoromethanesulfonyl)imidide type (the alkyl group being able to be an n-propyl group or an n-butyl group), because of their good cycling performances in a Li-ion system, as explained by Kim et al. In *J. Power Sources,* 199 (2012) 239-246.

However, in the battery field, the limiting point of these ionic liquids remains their high viscosity and their incompatibility vis-à-vis certain electrode materials, as is the case with graphite, which gives rise to a limitation of the performances of the battery in terms of cycling, cycling commonly designating the number of charging/discharging cycles that can be carried out by a battery. This phenomenon relates in particular to the electrochemical exfoliation involved when a graphite electrode is put in contact with an ionic liquid. Such a phenomenon was in particular described by Lu et al. In *ACS nano,* 3, 8, 2367-2375, in order to easily obtain nanoparticles of carbon and graphene from graphite.

In order to design an electrolyte based on ionic liquids having good cycling performance, some authors have had recourse to electrolyte additives, the particular reactivity of which makes it possible to stabilise the functioning of an electrochemical cell. The majority of electrolyte additives have the ability to form a protective deposit (SEI) on the surface of the electrodes, as is the case with vinylidene carbonate used for this purpose by Holzapfel et al. (Carbon, 47 (2005) 1488-1498) in their formulations of electrolytes based on ionic liquids.

Thus, in the light of what exists, the authors of the present invention set out to develop novel electrolytes which, apart from having good ionic conductivity, affords stabilisation of the electrode/electrolyte interface, in particular when these electrolytes are used in an electrochemical storage device comprising an electrode comprising graphite. These novel electrolytes, once incorporated in these devices, must also help to minimise the loss of capacity during cycling and good efficiency of restitution of the energy stored during charging (that is to say, in other words, good coulombic efficiency).

DISCLOSURE OF THE INVENTION

The invention thus relates to an electrolyte comprising at least one lithium salt and at least two ionic liquids, at least one of which is an ionic liquid resulting from the association of at least one cation complying with the following formula (I):

In which:
  $R^1$ is an acyclic hydrocarbon group;
  n is an integer ranging from 0 to 3;
  m is an integer ranging from 1 to 4;
  and at least one Y anion.

It is clear, from the above formulation, that the aforementioned lithium salt is not an ionic liquid and that the two ionic liquids are distinct ionic liquids, at least one of which is an ionic liquid resulting from the association of a cation of formula (I) and at least one Y anion.

It is clear that the cation or cations of formula (I) and the Y anion or anions are associated so as to provide the electroneutrality of the resulting ionic liquid (in other words, an ionic liquid wherein the positive charge or charges of said cation or cations balance the negative charge or charges of said anion or anions).

More explicitly, the cation of formula (I) may correspond, according to the values of n, to one of the following formulae:

*for n = 0, the following formula (Ia):

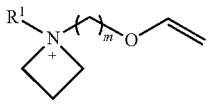
(Ia)

*for n = 1, the following formula (Ib):

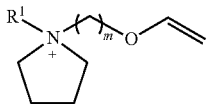
(Ib)

*for n = 2, the following formula (Ic):

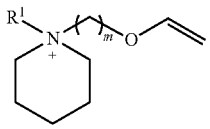
(Ic)

*for n = 3, the following formula (Id):

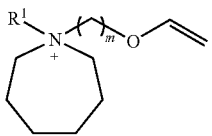
(Id)

Advantageously, one of the ionic liquids of the electrolytes of the invention is an ionic liquid in which the cation is a cation of formula (I) with n being equal to 1 (that is to say, in other words, a cation of formula (Ib)).

The group $R^1$ is an acyclic hydrocarbon group and more specifically it may be an acyclic hydrocarbon group, linear or branched, such as an alkyl group, comprising from 1 to 4 carbon atoms. Even more specifically, the group $R^1$ may be a group of formula $-C_pH_{2p+1}$, with p being an integer ranging from 1 to 4, for example, a methyl group, an ethyl group, a n-propyl group, an isopropyl group, a n-butyl group, an isobutyl group or a tert-butyl group.

By way of example, $R^1$ may be a methyl group.

By way of example, m may be equal to 2.

The Y anion may be an anion (in other words, the counter ion associated with the cation of formula (I)) chosen from halide anions (for example, chloride, bromide or iodide), a nitrate anion, a phosphate anion, imidide anions and more specifically a nitrate anion, a phosphate anion or an imidide anion.

More specifically:
when the anion is a nitrate anion, this complies with the formula $NO_3^-$;
when the anion is a phosphate anion, this complies with the formula $PO_4^{3-}$;
when the anion is an imidide anion, this means, conventionally, that it comprises an imide radical, the negative charge of which is carried by the nitrogen atom, said nitrogen atom being bonded to two carbonyl groups or two sulfonyl groups, said imide radical being able to be represented by one of the following formulas (II) and (III):

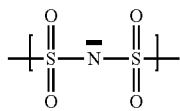
(II)

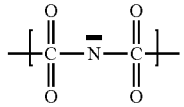
(III)

the brackets indicating that the $-SO_2-$ and $-CO_2-$ groups are bonded to other groups.

Advantageously, the anion is an imide anion, the negative charge of which is carried by the nitrogen atom, said nitrogen atom being bonded to sulfonyl groups, such an anion being able to be represented by the following general formula (II'):

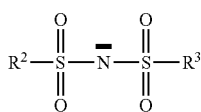
(II')

In which $R^2$ and $R^3$ represent, independently of one another, a fluorine atom or a perfluorocarbon group.

More specifically, $R^2$ and $R^3$ may represent, both, a fluorine atom or, both, a perfluorocarbon group, for example a perfluoromethyl group $-CF_3$.

Particular imide anions meeting these specificities are those of the following formulae (IV) and (V):

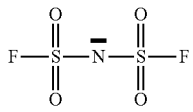
(IV)

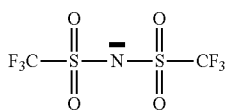
(V)

these imide ions being able to be termed respectively bis(fluorosulfonyl)imidide and bis(trifluoromethanesulfonyl)imidide.

More specifically again, one of the ionic liquids of the electrolytes of the invention is an ionic liquid in which the cation is a cation of formula (I) with n equal to 1 (that is to say, in other words, a cation of formula (Ib)) with $R^1$ corresponding to a methyl group and m being equal to 2 and the imidide anion being a bis(fluorosulfonyl)imidide or bis(trifluoromethanesulfonyl)imidide anion.

In this case, the cation complies with following formula (IIb):

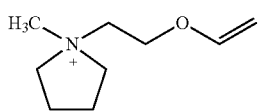
(IIb)

These ionic liquids thus result from the association of a cation of formula (Iib) and an anion of formula (IV) or (V), said ionic liquids complying with the following respective formulae (VI) and (VII):

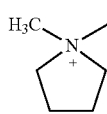 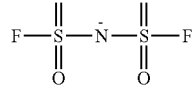
(VI)

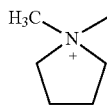 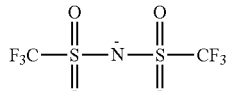
(VII)

these ionic liquids being able to be termed respectively N-(methyl)-(2-vinyloxyethyl)pyrrolidinium bis(fluorosulfonyl)imidide and N-(methyl)-(2-vinyloxyethyl)pyrrolidinium bis(trifluoromethanesulfonyl)imidide.

As mentioned above, at least one of the ionic liquids is an ionic liquid resulting from the association of at least one cation complying with formula (I) defined above and a Y anion, this or these ionic liquids representing, advantageously, 5% to 20% of the total volume of the ionic liquids present in the electrolyte, which, in this case, means that the electrolyte comprises at least one other ionic liquid the definition of which does not comply with the one for which the cation complies with formula (I) above and the anion is a Y anion.

Thus, in the electrolytes of the invention, at least one of the ionic liquids may be an ionic liquid different from those for which the cation is a cation of formula (I) as defined above and the anion is a Y anion.

More specifically, in the electrolytes of the invention, at least one of the ionic liquids is an ionic liquid resulting from the association of a phosphonium, sulfonium, azetidinium, pyrrolidinium or piperidinium cation and a halide, phosphate, nitrate or imidide anion, it being understood that, when the cation is an azetidinium, pyrrolidinium or piperidinium cation, the cation does not comply with formula (I) defined above.

Preferably, the anion is an imidide anion.

Preferably, the cation is a pyrrolidinium or piperidinium cation.

When the cation is an azetidinium, pyrrolidinium or piperidinium cation, it is understood that the cation does not comply with the aforementioned formula (I). Furthermore, advantageously, this cation does not comprise an ethylenic group.

Such a cation may comply with the following formula (VIII):

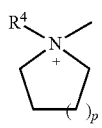
(VIII)

In which:
$R^4$ is an acyclic hydrocarbon group; and
p is an integer ranging from 0 to 2.

More explicitly, the cation of formula (VIII) may, according to the values of p, correspond to one of the following formulae:

*for p = 0, a specific azetidinium cation of the following formula (VIIIa):

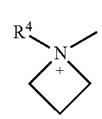
(VIIIa)

*for p = 1, a specific pyrrolidinium cation of the following formula (VIIIb):

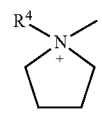
(VIIIb)

*for p = 2, a specific piperidinium cation of the following formula (VIIIc):

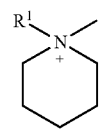
(VIIIc)

As for the anions, they may comply with the same definitions as those mentioned above with regard to the ionic liquids comprising a cation of formula (I).

Advantageously, one of the ionic liquids of the electrolytes of the invention is an ionic liquid in which the cation is a cation of formula (VIII) with p being equal to 1 (that is to say, in other words, a cation of formula (VIIIb)).

The group $R^4$ is an acyclic hydrocarbon group and more specifically it may be an acyclic hydrocarbon group, linear or branched, such as an alkyl group, comprising 1 to 4 carbon atoms. Even more specifically, the group $R^4$ may be a group of formula $—C_pH_{2p+1}$, with p being an integer ranging from 1 to 4, for example, a methyl group, an ethyl group, a n-propyl group, un isopropyl group, a n-butyl group, an isobutyl group or a tert-butyl group.

By way of example, $R^4$ may be an n-propyl group.

More specifically again, one of the ionic liquids of the electrolytes of the invention is an ionic liquid in which the cation is a cation of formula (VIII) with p being equal to 1 (that is to say, in other words, a cation of formula (VIIIb)) with $R^4$ corresponding to an n-propyl group and the imidide ion is a bis(trifluoromethanesulfonyl)imidide anion.

In this case, the cation complies with the following formula (IX):

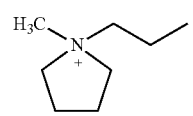
(IX)

This ionic liquid thus results from the association of a cation of formula (IX) and an anion of formula (V), said ionic liquid complying with the following formula (X):

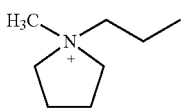 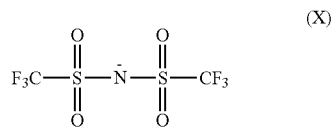 (X)

this ionic liquid being able to be to be termed N,N-(methyl)-(propyl)-pyrrolidinium bis(trifluoromethanesulfonyl)imidide.

Furthermore, the electrolytes of the invention comprise at least one lithium salt.

By way of examples of a lithium salt, mention can be made of lithium hexafluorophosphate ($LiPF_6$), lithium tetrafluoroborate ($LiBF_4$), lithium bis(trifluoromethanesulfonyl)imidide (known by the abbreviation LiTFSI), lithium hexafluoroarsenate ($LiAsF_6$), lithium nitrate ($LiNO_3$) or lithium perchlorate ($LiClO_4$).

The lithium salt may be included in the electrolytes of the invention to the extent of 0.1 to 2 moles of salt per litre of ionic liquids.

According to one embodiment of the invention, particular electrolytes of the invention may comprise or even consist solely of:
- an ionic liquid resulting from the association of at least one cation complying with formula (I) as defined above and at least one Y anion (for example an ionic liquid resulting from the association of a cation of formula (Ib) as defined above and an imidide anion);
- an ionic liquid different from those for which the cation is a cation of formula (I) as defined above and the anion is a Y anion (for example an ionic liquid resulting from the association of a cation of formula (VIIIb) as defined above and an imidide anion); and
- a lithium salt.

More specifically, a particular electrolyte according to the invention is an electrolyte comprising:
- an ionic liquid of formula (VI) as defined above;
- an ionic liquid of formula (X) as defined above;
- a lithium bis(trifluoromethanesulfonyl)imidide salt.

The electrolytes of the invention are particularly advantageous for electrochemical storage systems, wherein one of the electrodes comprises graphite. This is because it appears that the particular functionality present in the electrolyte (more precisely the vinyloxy function present in the cation of formula (I)) is able to polymerise on the surface of an electrode comprising graphite and thus generate a protective layer, so as to limit or even eliminate the phenomenon of exfoliation inherent in the putting of an ionic liquid in contact with graphite.

Furthermore, by means of this vinyloxy function that comprises free pairs at the oxygen atom, it is clear that the protective layer formed on the surface of the electrode also has good suitability for conveying lithium ions in its thickness. This phenomenon results in a real capacity of the electrochemical storage system closer to the nominal capacity of an electrode comprising graphite, in comparison with an electrolyte comprising, as an ionic liquid, solely a conventional ionic liquid.

Thus the invention also relates to an electrochemical storage device (for example a battery or an accumulator) comprising at least one cell comprising a positive electrode and a negative electrode separated from one another by a separator comprising an electrolyte according to the invention. More specifically, at least one of said electrodes is an electrode comprising, as active material, graphite.

Before going into more detail in the description of the electrochemical storage devices, the following definitions are specified.

Positive electrode means, conventionally, above and hereinafter, the electrode that serves as a cathode when the accumulator is supplying current (that is to say when it is in the process of discharging) and which serves as an anode when the accumulator in the process of charging.

Negative electrode means, conventionally, above and hereinafter, the electrode that serves as an anode when the accumulator is supplying current (that is to say when it is in the process of discharging) and which serves as a cathode when the accumulator is in the process of charging.

It is stated that each of the electrodes comprises an active material, that is to say a material that is directly involved in the reactions of insertion and deinsertion of the lithium during the charging or discharging reactions.

Apart from the presence of an active material, the electrode may comprise a polymer binder, such as polyvinylidene fluoride (known by the abbreviation PVDF), a mixture of carboxymethylcellulose (known by the abbreviation CMC) with a latex of the styrene-butadiene type (known by the abbreviation SBR) or with polyacrylic acid (known by the abbreviation PAA) as well as one or more electrically conductive adjuvants, which may be carbon materials such as carbon black.

Thus, from a structural point of view, the electrode may be in the form of a composite material comprising a matrix made from a polymeric binder or binders such as PVDF (for example to the extent of 1% to 10% of the ink deposited on the collector and precursor of the composite material), within which fillers are dispersed consisting of the active material (for example to the extent of 80% to 95% by mass of the ink disposed on the collector and precursor of the composite material) and optionally the electrically conductive adjuvant or adjuvants, such as carbon black (for example, to the extent of 1% to 8% of the mass of the ink deposited on the collector and precursor of the composite material), said composite material being deposited on a current collector.

The current collector may be a copper collector when the electrode is a negative electrode, while the current collector may be an aluminium collector when the electrode is a positive electrode.

More specifically, the electrode comprising graphite may be the negative electrode, in which case the electrochemical storage device may advantageously be an accumulator of the lithium-ion type.

In this case, the positive electrode may comprise, as active material, $LiMnO_2$, $LiMn_2O_4$, $LiCoO_2$, $LiNiO_2$, $LiNi_{1-x}Mn_{1+x}O_4$ with $0<x<1$, $LiNi_{1-x}Co_xO_2$ with $0<x<1$, $LiNi_xMn_yCo_zO_2$ with $0<x,y,z<1$ and $x+y+z=1$ or $LiFePO_4$.

According to another variant, the electrode comprising graphite may be the positive electrode.

In this case, the negative electrode may be a metal foil, such as lithium foil, which means in this case that the electrode will not be in the form of a composite material.

Alternatively, the negative electrode may comprise, as active material, $LiTiO_2$ or $Li_4Ti_5O_{12}$, this negative electrode being able in this case to be in the form of a composite material, as defined above.

The separator may be made from a porous material, such as a polymer material or a glass-fibre material, able to accommodate in its pores the electrolytes of the invention. Naturally the separator must be wettable and insoluble in the electrolytes of the invention. An example of a separator may be Celgard 2400®.

More specifically, a device according to the invention is a device in which the positive electrode comprises graphite as active material and in which the negative electrode is a metallic lithium electrode.

The electrolyte for its part may be an electrolyte comprising:
- an ionic liquid of formula (VI) as defined above;
- an ionic liquid of formula (X) as defined above;
- a lithium bis(trifluoromethanesulfonyl)imidide salt.

With this type of device, the following performances can be achieved:
- First-discharge capacity greater than 25% of the theoretical capacity of the negative electrode;
- Loss of capacity over 10 cycles of less than 50% of the capacity of the first cycle;
- Coulombic efficiency (energy restored at the discharge) of at least 90% at the tenth cycle.

Other features and advantages of the invention will emerge from the additional description that follows and which relates to particular embodiments.

Naturally this additional description is given only by way of illustration of the invention and under no circumstances constitutes a limitation.

DETAILED DISCLOSURE OF PARTICULAR EMBODIMENTS

Example 1

This example illustrates the preparation of an electrolyte according to the invention.

This example illustrates the preparation of an electrolyte according to the invention.

This electrolyte is produced in a glove box by combining 0.9 ml of N,N-methylpropylpyrrolidinium bis(trifluoromethanesulfonyl)imidide of the following formula (X):

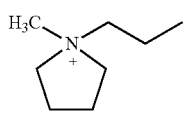 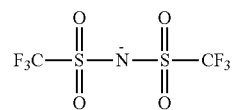 (X)

with 0.1 mL of N,N-methyl-(2-vinyloxyethyl)pyrrolidinium bis(fluorosulfonyl)imidide of the following formula (VI):

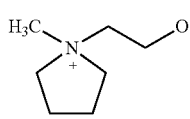 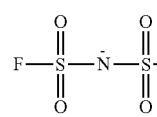 (VI)

and 0.2871 g of lithium bis(trifluoromethanesulfonyl)imidide (LiTFSI).

Comparative Example 1

This example illustrates the preparation of an electrolyte not in accordance with the invention.

This electrolyte is produced in a glove box by combining 1.0 ml of N,N-methylpropylpyrrolidinium bis(trifluoromethanesulfonyl)imidide with 0.2871 g of lithium bis(trifluoromethanesulfonyl)imidide (LiTFSI).

Example 2

In this example, the performances of the electrolytes mentioned in example 1 and comparative example 1 are evaluated for an application in electrochemical storage. To do this, test cells (more specifically, button batteries to format 2032) are assembled in advance in a glove box in accordance with the following protocol:

- Placing of a 2032 battery casing (bottom cap) provided with a seal;
- Insertion of a stainless steel disc with a diameter suited to the inside diameter of the battery;
- Insertion of a 16 mm diameter disc of a positive electrode comprising, as active material, graphite (96%), Super P carbon black (1%), a binder comprising carboxymethylcellulose (1%) and a styrene/butadiene rubber (2%), with a capacity of 1.4 mAh/cm$^2$, the face of which comprising material is turned upwards;
- Insertion of a 16.5 mm diameter Whatman separator previously soaked in 150 µL of one of the aforementioned electrolytes;
- Insertion of a 16 mm diameter lithium disc, which serves as a negative electrode;
- Insertion of a second stainless steel disc and a compression spring;
- Addition of a top cap and then crimping by pressing the whole.

Once produced, the button batteries are introduced into a cycling bench of the Biologic™ type positioned in an oven. The following cycling conditions are then applied:

- Test temperature set at 45° C.;
- Performance of 10 successive charging/discharging cycles by chronopotentiometry in accordance with the following parameters:
  - Charging from 1.5 V to 0.02 V in 10 hours (charging rate C/10);
  - Discharging from 0.02 V to 1.5 V in 10 hours (discharge rate D/10);
- Performance of 10 successive charging/discharging cycles by chronopotentiometry in accordance with the following parameters:
  - Charging from 1.5 V to 0.02 V in 5 hours (charging rate C/5);
  - Discharging from 0.02 V to 1.5 V in 5 hours (discharge rate D/5);

The change in the battery capacities measured in this protocol, as well as the efficiency of restitution of the stored energy (coulombic efficiency), are retranscribed in the following tables for the various electrolytes tested.

*Cyclings at 45° C., at a discharge rate of D/10 (complete discharge in 10 hours)

| Electrolyte | % of the capacity of the graphite electrode* (cycle 1/cycle 10) | Loss of capacity** (%) | Coulombic efficiency*** (%) |
|---|---|---|---|
| Comparative example 1 | 3.2/0.9 | 71.7 | 97 |
| Example 1 | 71.4/71.4 | 0 | 100 |

*capacity of the graphite electrode = 1.4 mAh/cm$^2$
**measured between cycles 1 and 10
***at cycle 10

*Cyclings at 45° C., at a discharge rate of D/5 (complete discharge in 5 hours)

| Electrolyte | % of the capacity of the graphite electrode* (cycle 1/cycle 10) | Loss of capacity** (%) | Coulombic efficiency*** (%) |
|---|---|---|---|
| Comparative example 1 | 0.7/0.6 | 15.2 | 99 |
| Example 1 | 70.3/69.3 | 1.5 | 100 |

*capacity of the graphite electrode = 1.4 mAh/cm$^2$
**measured between cycles 1 and 10
***at cycle 10

With regard to these results, by virtue of the cell capacity as close as possible to the capacity of the graphite electrode (up to 71.4%), the low losses of capacity measured (up to 0% over 10 cycles) and the coulombic efficiency greater than 90%, the electrolyte of the invention has performances quite different compared with electrolytes based on conventional ionic liquids, which confirms the advantage presented by the electrolytes of the invention.

What is claimed is:

1. An electrolyte comprising at least one lithium salt, a first ionic liquid and a second ionic liquid, the first ionic liquid comprising a cation of formula (I):

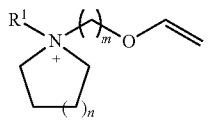
(I)

in which:
R$^1$ is an acyclic hydrocarbon group;
n is an integer ranging from 0 to 3;
m is an integer ranging from 1 to 4;
and at least one associated anion Y.

2. The electrolyte according to claim 1, wherein the cation of formula (I) is of formula (Ib):

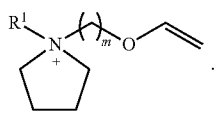
(Ib)

3. The electrolyte according to claim 1, wherein R$^1$ is an alkyl group comprising 1 to 4 carbon atoms.

4. The electrolyte according to claim 1, wherein m is equal to 2.

5. The electrolyte according to claim 1, wherein the at least one associated anion Y is chosen from a nitrate anion, a phosphate anion or an imidide anions.

6. The electrolyte according to claim 5, wherein the at least one associated anion Y is chosen the imidide anions.

7. The electrolyte according to claim 6, wherein the imidide anion is of formula (II'):

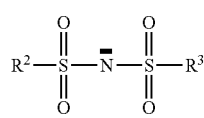
(II')

wherein R$^2$ and R$^3$ represent, independently of one another, a fluorine atom, a perfluorocarbon group.

8. The electrolyte according to claim 7, wherein the imidide anion is selected from formula (IV) or formula (V):

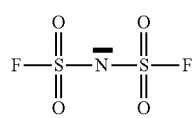
(IV)

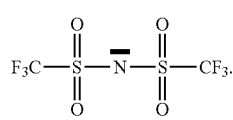
(V)

9. The electrolyte according to claim 1, wherein the first ionic liquid comprises associated ions according to one of wherein the first ionic liquid comprises the cation associated with the at least one associated anion Y according to formula (VI) or formula (VII): formula (VI) or formula (VII):

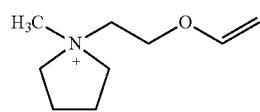 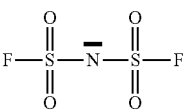
(VI)

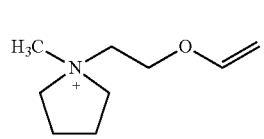 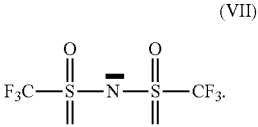
(VII)

10. The electrolyte according to claim 1, wherein the second ionic liquid comprises a cation of the second ionic liquid selected from the group consisting of phosphonium, sulfonium, azetidinium, pyrrolidinium or piperidinium and an associated anion of the second ionic liquid selected from the group consisting of halide, phosphate, nitrate or imidide.

11. The electrolyte according to claim 10, wherein the cation of the second ionic liquid is selected from a pyrrolidinium cation and a piperidinium cation.

12. The electrolyte according to claim 11, wherein the cation of the second ionic liquid is of formula (VIII):

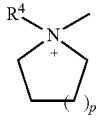
(VIII)

in which:
$R^4$ is an acyclic hydrocarbon group; and
p is an integer ranging from 0 to 2.

13. The electrolyte according to claim 12, wherein the cation of the second ionic liquid is of formula (VIIIb):

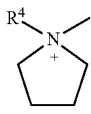
(VIIIb)

wherein $R^4$ is an acyclic hydrocarbon group.

14. The electrolyte according to claim 10, wherein the associated anion of the second ionic liquid is an imidide anion.

15. The electrolyte according to claim 10, wherein the the cation of the second ionic liquid and the associated anion of the second ionic liquid are of formula (X):

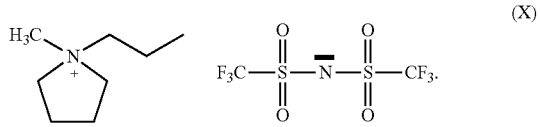
(X)

16. The electrolyte according to claim 1, wherein the lithium salt is chosen from lithium hexafluorophosphate ($LiPF_6$), lithium tetrafluoroborate ($LiBF_4$), lithium bis(trifluoromethanesulfonyl)imidide (LiTFSI), lithium hexafluoroarsenate ($LiAsF_6$), lithium nitrate ($LiNO_3$) or lithium perchlorate ($LiClO_4$).

17. An electrochemical storage device comprising at least one cell comprising a positive electrode and a negative electrode separated from one another by a separator comprising the electrolyte as defined according to claim 1.

18. The electrochemical storage device according to claim 17, wherein at least one of the positive electrode and/or the negative electrode comprises graphite as an active material.

* * * * *

UNITED STATES PATENT AND TRADEMARK OFFICE
CERTIFICATE OF CORRECTION

| | | |
|---|---|---|
| PATENT NO. | : 11,335,954 B2 | Page 1 of 1 |
| APPLICATION NO. | : 16/495197 | |
| DATED | : May 17, 2022 | |
| INVENTOR(S) | : Stephane Cadra et al. | |

It is certified that error appears in the above-identified patent and that said Letters Patent is hereby corrected as shown below:

On the Title Page (*), "Notice: Subject to any disclaimer, the term of this patent is extended or adjusted under 35 U.S.C. 154(b) by 225 days.", should read -- Notice: Subject to any disclaimer, the term of this patent is extended or adjusted under 35 U.S.C. 154(b) by 225 days. This patent is subject to a terminal disclaimer. --.

(45), "Date of Patent: May 17, 2022", should read -- Date of Patent: *May 17, 2022 --.

Signed and Sealed this
Twentieth Day of December, 2022

Katherine Kelly Vidal
*Director of the United States Patent and Trademark Office*